US00PP27947P2

(12) United States Plant Patent
Hartman

(10) Patent No.: US PP27,947 P2
(45) Date of Patent: Apr. 25, 2017

(54) ***CALADIUM* PLANT NAMED 'ALLURE'**

(50) Latin Name: *Caladium×hortulanum*
Varietal Denomination: Allure

(71) Applicant: Robert Dale Hartman, Lake Placid, FL (US)

(72) Inventor: Robert Dale Hartman, Lake Placid, FL (US)

( * ) Notice: Subject to any disclaimer, the term of this patent is extended or adjusted under 35 U.S.C. 154(b) by 0 days.

(21) Appl. No.: 14/998,543

(22) Filed: Jan. 16, 2016

(51) Int. Cl.
*A01H 5/02* (2006.01)

(52) U.S. Cl.
USPC ..... Plt./373

(58) Field of Classification Search
USPC ..... Plt./373
See application file for complete search history.

*Primary Examiner* — Annette Para
(74) *Attorney, Agent, or Firm* — C. A. Whealy

(57) ABSTRACT

A new and distinct cultivar of *Caladium* plant named 'Allure', characterized by its tall, upright and uniformly mounded plant habit; vigorous growth habit and very rapid growth rate; fancy-type leaves with white-colored centers with dark green-colored venation and thin dark green-colored margins; relatively high yield of the largest grade tubers; and above average tolerance to *Xanthomonas* Leaf Spot.

4 Drawing Sheets

Botanical designation: *Caladium×hortulanum.*
Cultivar denomination: 'ALLURE'.

BACKGROUND OF THE INVENTION

The present invention relates to a new and distinct cultivar of *Caladium* plant, botanically known as *Caladium×hortulanum*, commercially referred to as a fancy leaf-type *Caladium* and hereinafter referred to by the name 'Allure'.

The objective of the Inventor's breeding program is to create new *Caladium* plants that have uniform plant habit, exceptional container and garden performance and attractive and unique leaf coloration.

The new *Caladium* plant originated from a cross-pollination made by the Inventor in April, 2009 in Avon Park, Fla. of *Caladium×hortulanum* 'Candidum Senior', not patented, as the female, or seed, parent with *Caladium×hortulanum* 'Candidum', not patented, as the male, or pollen, parent. The new *Caladium* plant was discovered and selected by the Inventor as a single plant within the progeny of the stated cross-pollination in a controlled outdoor nursery environment in Zolfo Springs, Fla. in September, 2010.

Asexual reproduction of the new *Caladium* plant by 'chipping' the tubers (cutting the tuber into segments with each segment containing an axillary bud and tuber cortical tissue) in a controlled outdoor nursery environment in Zolfo Springs, Fla. since April, 2011 has shown that the unique features of this new *Caladium* plant are stable and reproduced true to type in successive generations of asexual reproduction.

SUMMARY OF THE INVENTION

Plants of the new *Caladium* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Allure'. These characteristics in combination distinguish 'Allure' as a new and distinct *Caladium* plant:

1. Tall in height, upright and uniformly mounded plant habit.
2. Vigorous growth habit and very rapid growth rate.
3. Fancy-type leaves with white-colored centers with dark green-colored venation and thin dark green-colored margins.
4. Relatively high yield of the largest grade tubers.
5. Above average tolerance to *Xanthomonas* Leaf Spot.

Plants of the new *Caladium* differ primarily from plants of the female parent, 'Candidum Senior', in the following characteristics:

1. Plants of the new *Caladium* and 'Candidum Senior' differ in leaf color as leaves of 'Candidum Senior' are greenish white in color with medium green-colored venation and thin green-colored margins.
2. Leaves of plants of the new *Caladium* and 'Candidum Senior' differ in undulation and rugosity as leaves of 'Candidum Senior' are more undulate and rugose than leaves of the new *Caladium.*
3. Plants of the new *Caladium* produce more tubers of the largest grade sizes than plants of 'Candidum Senior'.

Plants of the new *Caladium* differ primarily from plants of the male parent, 'Candidum', in the following characteristics:

1. Plants of the new *Caladium* and 'Candidum' differ in leaf color as leaves of 'Candidum' have distinct green-colored venation with white-colored interveinal areas; developing leaves of 'Candidum' are mostly green in color with white-colored flecks.
2. Plants of the new *Caladium* and 'Candidum' differ in tolerance to *Xanthomonas* Leaf Spot as plants of 'Candidum' are more susceptible to damage resulting from *Xanthomonas* Leaf Spot than plants of the new *Caladium.*

3. Plants of the new *Caladium* produce more tubers of the largest grade sizes than plants of 'Candidum'.

Plants of the new *Caladium* can be compared to plants of *Caladium×hortulanum* 'White Christmas', not patented. In side-by-side comparisons, plants of the new *Caladium* differ primarily from plants of 'White Christmas' in the following characteristics:

1. Plants of the new *Caladium* and 'White Christmas' differ in leaf color as leaves of 'White Christmas' have distinct dark green-colored venation with white-colored interveinal areas that are often tinged with pink and dark green-colored borders.
2. Plants of the new *Caladium* and 'White Christmas' differ in tolerance to *Xanthomonas* Leaf Spot as plants of 'White Christmas' are more susceptible to damage resulting from *Xanthomonas* Leaf Spot than plants of the new *Caladium*.
3. Plants of the new *Caladium* produce more tubers of the largest grade sizes than plants of 'White Christmas'.

Plants of the new *Caladium* can also be compared to plants of *Caladium×hortulanum* 'Florida Moonlight', disclosed in U.S. Plant Pat. No. 14,565. In side-by-side comparisons, plants of the new *Caladium* differ primarily from plants of 'Florida Moonlight' in the following characteristics:

1. Plants of the new *Caladium* and 'Florida Moonlight' differ in leaf color as leaves of 'Florida Moonlight' have greenish white-colored leaves and venation.
2. Plants of the new *Caladium* and 'Florida Moonlight' differ in leaf petiole color as leaf petioles of 'Florida Moonlight' are tan pink in color with greenish brown-colored stippling, streaks and tessellations.

BRIEF DESCRIPTION OF THE PHOTOGRAPHS

The accompanying photographs illustrate the overall appearance of the new *Caladium* plant showing the colors as true as it is reasonably possible to obtain in colored reproductions of this type. Colors in the photographs may differ slightly from the color values cited in the detailed botanical description which accurately describe the colors of the new *Caladium* plant.

The photograph on the first sheet is a side perspective view of a typical plant of 'Allure' in a container and grown in a shadehouse (tuber not de-eyed).

The photograph at the top of the second sheet is a comparison view of typical potted plants of the female parent, 'Candidum Senior' (left), 'Allure' (center) and the male parent, 'Candidum' (right).

The photograph at the bottom of the second sheet is a comparison view of typical potted plants of 'White Christmas' (left), 'Allure' (center) and 'Florida Moonlight' (right).

The photograph at the top of the third sheet is a comparison view of typical plants of 'Allure' grown in containers; the plant on the left has not had its tuber de-eyed and the plant on the right has had its tuber de-eyed prior to planting.

The photograph at the bottom of the third sheet is a side perspective view of typical plants of 'Allure' grown in an open field.

The photograph at the top of the fourth sheet is a close-up view of a typical freshly-harvested tuber and roots of 'Allure'.

The photograph at the bottom of the fourth sheet is a close-up view of a typical inflorescence of 'Allure'.

DETAILED BOTANICAL DESCRIPTION

The aforementioned photographs and following observations and measurements describe plants grown in 15-cm containers in a polypropylene-covered shadehouse (30% light reduction) in Avon Park, Fla. and plants grown in ground beds under full sunlight conditions in an outdoor nursery in Crewsville, Fla. The plants were grown under cultural practices typical of commercial shadehouse and outdoor nursery production. During the production of the shadehouse-grown plants, day temperatures ranged from about 28° C. to 33° C., night temperatures ranged from about 22° C. to 25° C. and light levels were about 8,000 foot-candles. During the production of the outdoor nursery-grown plants, day temperatures ranged from about 29° C. to 35° C., night temperatures ranged from about 23° C. to 26° C. and light levels ranged from about 10,000 to 12,000 foot-candles. Plants grown in the shadehouse were five weeks old (vegetative plant photographs and description) and twelve weeks old (inflorescence photograph and description), and plants grown in the outdoor nursery were eight months old when the photographs and the detailed description were taken. In the following description, color references are made to The Royal Horticultural Society Colour Chart, 2001 Edition, except where general terms of ordinary dictionary significance are used.

Botanical classification: *Caladium×hortulanum* 'Allure'.

Parentage:

*Female, or seed, parent.*—*Caladium×hortulanum* 'Candidum Senior', not patented.

*Male, or pollen, parent.*—*Caladium×hortulanum* 'Candidum', not patented.

Propagation:

*Type.*—By "chipping" the tubers.

*Time to initiate roots, summer.*—About seven to ten days at temperatures about 32° C.

*Time to initiate roots, winter.*—About two to three weeks at temperatures about 24° C.

*Tuber description* (*outdoor nursery-grown plants*).—Appearance: Multi-segmented and somewhat flattened; individual segments ovate, elliptic or irregular in shape. Height: About 4.7 cm. Diameter: About 6.5 cm to 10 cm. Segment height: About 1.7 cm to 3.3 cm. Segment diameter: About 1.6 cm to 3.4 cm. Axillary buds, height: About 4 mm to 8 mm. Texture: Thick, starchy; somewhat brittle. Color: Epidermis, freshly-harvested: Close to N170D; outer skin, close to 199C. Epidermis, dried: Close to 200A. Cortical tissue: Close to 158C. Axillary buds: Close to 49C. Root description: Thick, fleshy contractile roots; color, close to 155C. Rooting habit: Low branching; medium density.

Plant description:

*Plant type.*—Herbaceous perennial; suitable as a potted plant in containers 15-cm to 25-cm and suitable as a landscape plant in shaded areas.

*Plant and growth habit.*—Tall in height, upright and uniformly mounded plant habit; vigorous and dense growth habit; very rapid growth rate, potted plants in finished or saleable form in about five weeks after planting tubers; leaf petioles and leaves arise from one or more growing points on tubers; petioles mostly upright and leaning outwardly with development.

*Plant height, from soil level to top of foliar plane, shadehouse-grown potted plants*.—About 32 cm to 36 cm.

*Plant height, from soil level to top of inflorescences, shadehouse-grown potted plants*.—About 38 cm.

*Plant diameter or spread, shadehouse-grown potted plants*.—About 44 cm to 52 cm.

*Number of shoots per plant, shadehouse-grown potted plants, tubers not de-eyed*.—About four develop per #1 tuber.

*Number of shoots per plant, shadehouse-grown potted plants, tubers de-eyed*.—About five to six develop per #1 tuber.

*Cataphylls, shadehouse-grown potted plants*.—Length: About 4 cm to 5.5 cm. Width: About 1 cm. Shape: Lanceolate. Apex: Acute. Base: Sheathing the stem. Color, inner surface: Close to N155B; colors and patterns on the outer surface are visible on the inner surface. Color, outer surface: Close to 156D tinged with close to 147D and marbled with close to 147A tinged with close to N200A; with development, color becoming closer to N199B and tinged with close to 187B to 187C.

Leaf description:

*Arrangement and type*.—Alternate; simple; fancy-type.

*Length, shadehouse-grown potted plants*.—About 19 cm to 34 cm.

*Width, shadehouse-grown potted plants*.—About 13 cm to 22 cm.

*Shape*.—Ovate.

*Apex*.—Acuminate to acute.

*Base*.—Sagittate to peltate.

*Margin*.—Entire; somewhat undulate with broad undulations.

*Texture, upper and lower surfaces*.—Smooth, glabrous.

*Luster, upper surface*.—Dull sheen.

*Luster, lower surface*.—Glaucous, dull sheen.

*Venation pattern*.—Pinnate.

*Color, shadehouse-grown potted plants*.—Developing leaves, upper surface: Main colors: Close to 157D and 155C. Margins: Close to 147A. Basal notch: Small in size, close to 187C. Midvein and primary venation: Close to 147A tinged with close to 139A. Secondary venation: Close to 147A and 147B. Developing leaves, lower surface: Main colors: Close to 157C, 157D and 155C. Margins: Close to 147B. Basal notch: Small in size, close to 187C. Midvein: Close to 147B to 147C. Primary venation: Close to 147B. Secondary venation: Close to 146B to 146C and 147C. Fully expanded leaves, upper surface: Main color: More white than 155C. Margins: Close to 147A. Basal notch: Small in size, close to 187B to 187C. Midvein and primary venation: Close to 147A tinged with close to 139A. Secondary venation: Close to 147B. Fully expanded leaves, lower surface: Main color: Close to 155C. Margins: Close to 147B to 147C. Basal notch: Small in size, close to 187B to 187C. Midvein: Close to 147C. Primary venation: Close to 147B. Lateral venation: Close to 146B to 146C and 147C.

*Petioles*.—Aspect: Initially upright and straight; with development, leaning outwardly; flexible. Length, shadehouse-grown potted plants: About 26 cm to 32 cm. Diameter, distally, shadehouse-grown potted plants: About 4.5 mm to 6.5 mm. Diameter, proximally, shadehouse-grown potted plants: About 6 mm to 10 mm. Texture: Smooth, glabrous; glaucous. Color, shadehouse-grown potted plants: When developing: Close to 159C and 199D streaked, stippled and tessellated with close to 199A and N199A. Fully developed: Close to 200A to 200B variably striped with close to 199A tinged with close to 147D; below the leaf and petiole junction, close to 147D and 146D variably tinged and streaked with close to 200B to 200C. Wing length, shadehouse-grown potted plants: About 4.3 cm to 6 cm. Wing diameter, shadehouse-grown potted plants: About 6 mm to 9 mm. Texture, inner and outer surfaces: Smooth, glabrous. Luster, inner and outer surfaces: Dull to somewhat glossy. Wing color, shadehouse-grown potted plants: Inner surface: Close to N155B; colors and patterns on the outer surface are visible on the inner surface. Outer surface: Close to 159D tinged with close to 147D; stippled, streaked and marbled with close to N200A tinged with close to 147A.

Inflorescence description: Inflorescences observed on twelve week-old shadehouse-grown potted plants.

*Inflorescence arrangement*.—Upright hooded spathes surrounding a columnar spadix borne on a tall upright scape; spadix with sessile, simple female and male flowers separated into two zones; female flowers develop on the proximal one-third of the spadix; male flowers develop on the distal two-thirds of the spadix; sterile flowers develop at junction of female and male flower zones; near this junction, the spathe constricts and surrounds and encloses the female flowers; spathe open and cupped around male flowers.

*Fragrance*.—Night-fragrant; sweet, jasmine-like with camphor note.

*Natural flowering season and flower longevity*.—Plants of the new *Caladium* typically flower during the spring and early summer in central Florida; flowers develop about twelve weeks after growth commences; inflorescences last about three days before fading; inflorescences persistent.

*Spathe*.—Length, overall: About 11.5 cm. Length, distal open portion: About 7.7 cm. Length, proximal closed portion: About 3.8 cm. Width, distal open portion: About 3.7 cm. Depth, distal open portion: About 2.8 cm. Width, at constriction: About 1.4 cm. Width, proximal closed portion: About 2.4 cm. Shape: Elliptic. Apex: Acuminate. Base: Obtuse. Margin: Entire. Texture, front and rear surfaces: Smooth, glabrous. Luster, front surface: Dull sheen. Luster, rear surface: Glaucous. Color, front surface: Distal open portion: Close to 155C; venation and margins faintly tinged with close to 157B; with development, color becoming closer to N199A. Proximal closed portion: Close to 139D; towards the base, lightly streaked and flushed with close to N186C; color does not change with development. Color, rear surface: Distal open portion: Close to 157C and 157D; center, tinged with close to 145C to 145D; color does not change with development. Proximal closed portion: Close to 138A and 138B with areas tinged with close to 147B to 147C; color does not change with development.

*Spadix*.—Length, overall: About 6.5 cm. Length, male flower zone: About 4 cm. Length, sterile zone: About 1.3 cm. Length, female flower zone: About 1.2 cm. Diameter, male flower zone: About 9 mm. Diameter, sterile flower zone: About 6 mm. Diameter, female flower zone: About 8.5 mm. Shape: Columnar to spindle-shaped. Apex: Acute to obtuse. Base: Obtuse. Aspect: Upright. Color, mature, male zone: Close to 158B. Color, mature, sterile zone: Close to 158D. Color, mature, female zone: Close to 155D and 158C. Male flowers: Quantity per spadix: About 96. Shape: Obovate. Height: About 3 mm. Diameter: About 3 mm to 3.5 mm. Pollen amount: Moderate. Pollen color: Close to 4C. Female flowers: Quantity per spadix: About 91. Shape: Obovate. Height: About 2.5 mm. Diameter: About 2 mm. Stigma color: Close to 155D. Ovary color: Close to 158C.

*Scape*.—Length: About 26.5 cm. Diameter: About 6.5 mm. Strength: Sturdy; flexible. Aspect: Mostly erect. Texture: Smooth, glabrous. Luster: Slightly glossy; below spathe, glaucous. Color: Close to 195D and 147D stippled, striped and streaked with close to 200A and 200B; just below spathe, close to 147B to 147C and tinged with close to 146C, faintly streaked and striped with close to 200A and 200B.

*Seeds and fruits*.—To date, seed and fruit development have not been observed on plants of the new *Caladium*.

Disease & pest tolerance: Plants of the new *Caladium* have been observed to have above average tolerance to *Xanthomonas* Leaf Spot. Plants of the new *Caladium* have been observed to have average tolerance to *Pythium* Root Rot. Plants of the new *Caladium* have not been observed to have resistance to pests and other pathogens common to *Caladium* plants.

Temperature tolerance: Plants of the new *Caladium* have been observed to be tolerant to temperatures ranging from about 7° C. to about 40° C. and are suitable for USDA Hardiness Zones 8A to 11. In cooler zones, tubers can be "lifted" prior to first freeze and stored in a cool dry environment overwinter for re-planting the following spring.

It is claimed:

1. A new and distinct *Caladium* plant named 'Allure' as illustrated and described.

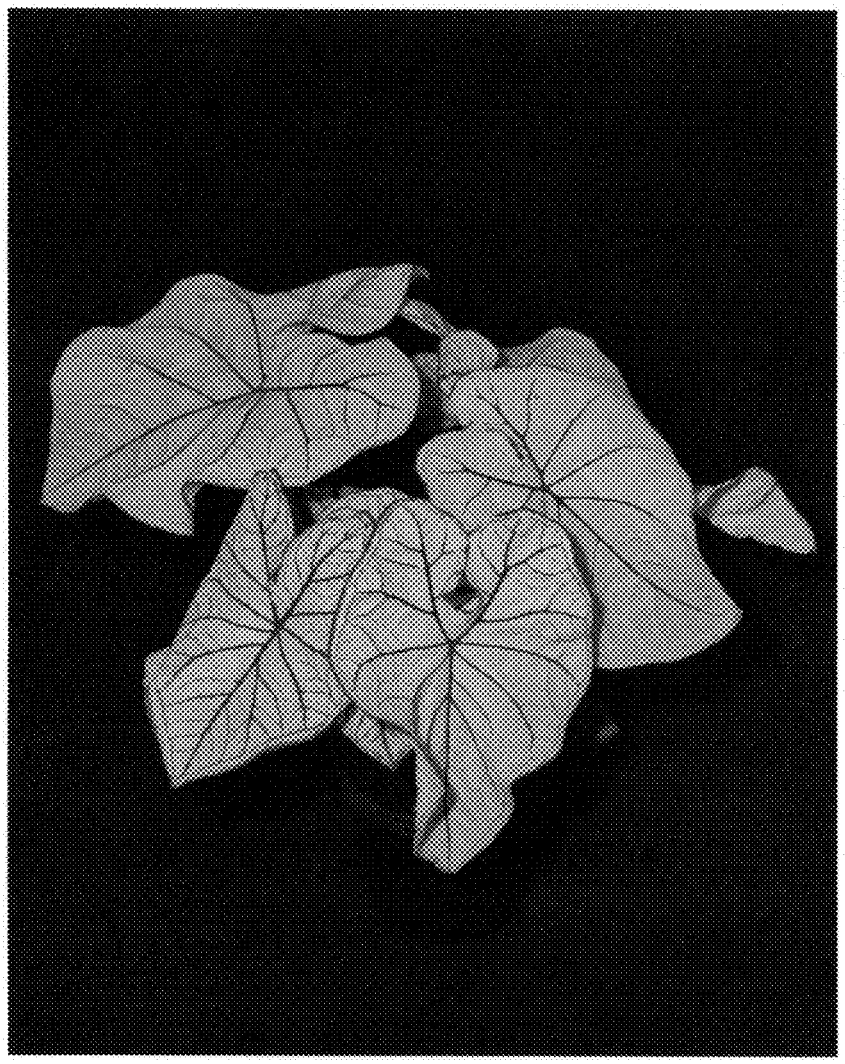

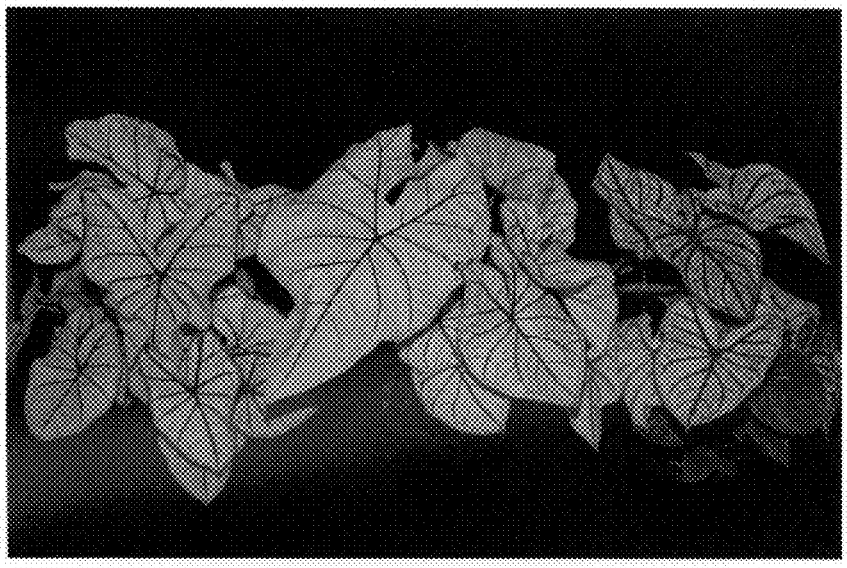
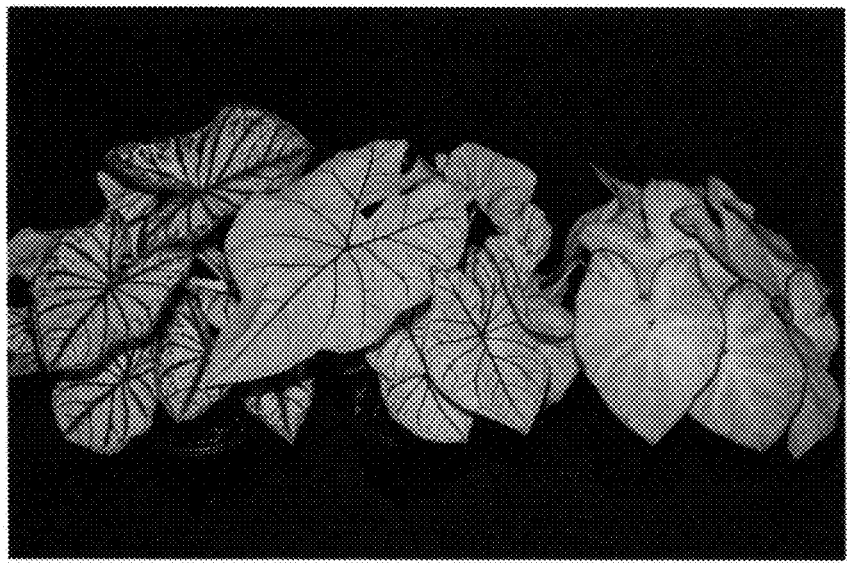

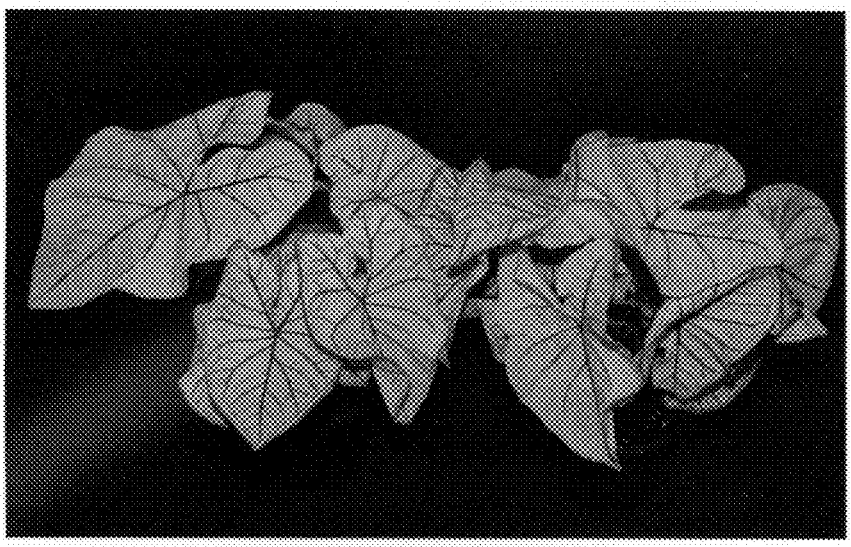
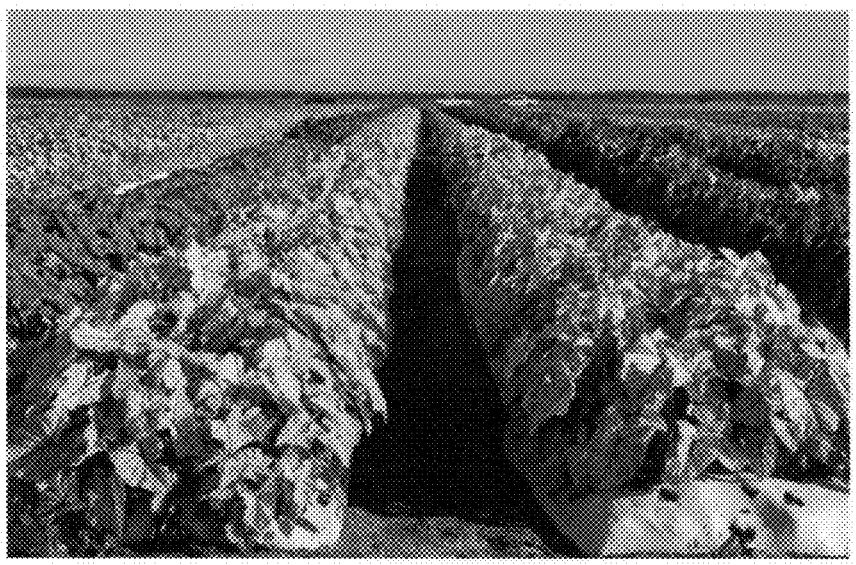

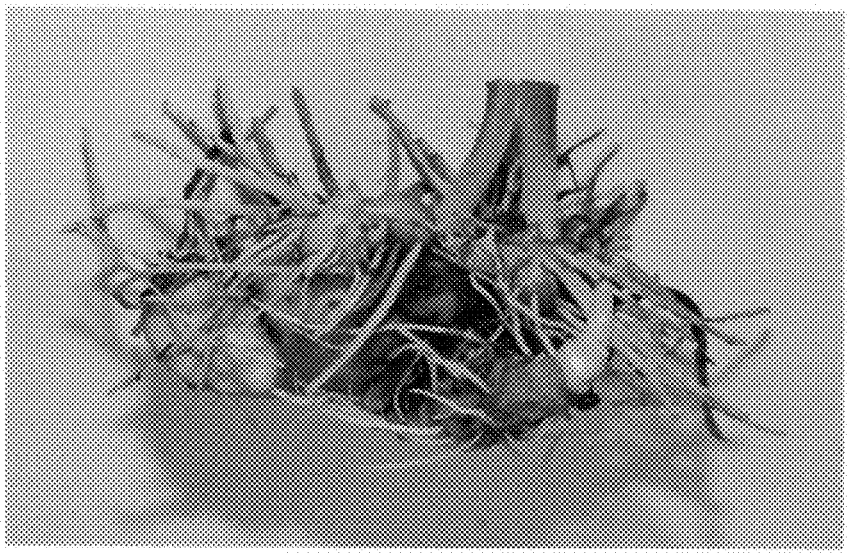
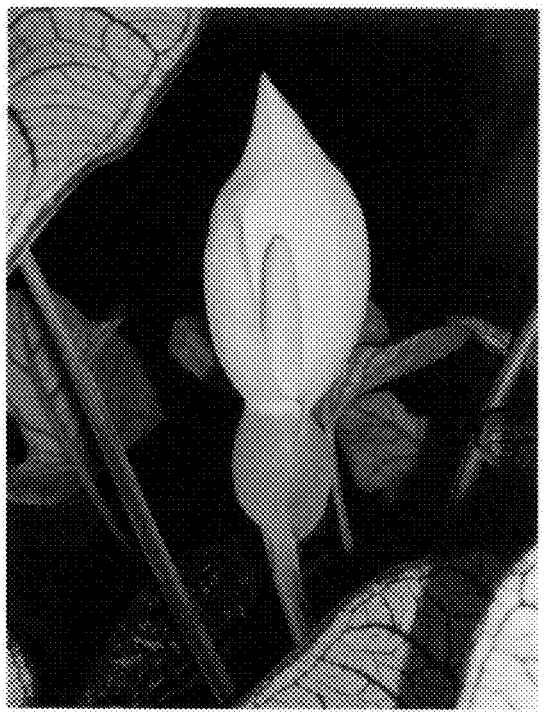

* * * * *